United States Patent [19]
Sperling

[11] Patent Number: 5,844,680
[45] Date of Patent: Dec. 1, 1998

[54] DEVICE AND PROCESS FOR MEASURING AND ANALYSING SPECTRAL RADIATION, IN PARTICULAR FOR MEASURING AND ANALYSING COLOR CHARACTERISTICS

[75] Inventor: Uwe Sperling, Geretsried, Germany

[73] Assignee: BYK-Gardner GmbH, Geretsried, Germany

[21] Appl. No.: 809,511

[22] PCT Filed: Sep. 24, 1995

[86] PCT No.: PCT/EP95/03789

§ 371 Date: Jun. 3, 1997

§ 102(e) Date: Jun. 3, 1997

[87] PCT Pub. No.: WO96/09524

PCT Pub. Date: Mar. 28, 1996

[30] Foreign Application Priority Data

Sep. 24, 1994 [DE] Germany .......................... 44 34 168.7

[51] Int. Cl.⁶ .................................................... G01J 3/40
[52] U.S. Cl. .................... 356/303; 356/323; 356/324; 356/302; 356/303
[58] Field of Search .................................. 356/303, 323, 356/324, 300, 302

[56] References Cited

U.S. PATENT DOCUMENTS

| | | | |
|---|---|---|---|
| 3,715,163 | 2/1973 | Mitchell | 356/323 |
| 4,111,556 | 9/1978 | Grisar et al. | 356/303 |
| 5,210,590 | 5/1993 | Landa et al. | 356/323 |

*Primary Examiner*—Frank G. Font
*Assistant Examiner*—Reginald A. Ratliff
*Attorney, Agent, or Firm*—Ohlandt, Greeley, Ruggiero & Perle

[57] ABSTRACT

A device and process for measuring and analyzing spectral radiation within a desired wavelength range. A number of radiation sources are provided, in combination with a sensor for detecting radiation within the desired wavelength range. The radiation sources are selected to have spectral characteristics that are linearly independent from one another, but overlap so that, in combination, the radiation sources generate radiation over the entire desired wavelength range. Alternatively, a single radiation source generating radiation over the entire desired wavelength range is provided in combination with a plurality of sensors that have spectral sensing characteristics that are linearly independent from one another, but overlap so that, in combination, the sensors sense radiation over the entire desired wavelength range. Further provided is a control unit that stores a number of calibration functions with linearly independent spectral characteristics, the control unit further receiving output values from the sensors to determine the spectral characteristics of the object being measured.

18 Claims, 7 Drawing Sheets

DEVICE AND PROCESS FOR MEASURING AND ANALYSING SPECTRAL RADIATION, IN PARTICULAR FOR MEASURING AND ANALYSING COLOR CHARACTERISTICS

FIELD OF THE INVENTION

The invention relates to an apparatus and a method for measuring and analysing spectral radiation. The term "spectral radiation" refers to radiation which spans a specific wavelength range. In particular, the invention relates to a device and a method for measuring and analysing the colour characteristics of passively or actively irradiating objects.

In the following, the problem to be solved by the invention and its solution will be described with reference to the example of an apparatus and a method for measuring and analysing of the spectral characteristics of colours, that is, of radiation which is in the visible wavelength range of between 380 and 780 nanometer (nm). The invention, however, is not restricted to the range of visible light but may also be used for radiation having a shorter or, as the case may be, longer wavelength.

The colour of surfaces is a fundamental characteristic of all objects which play a role in daily life, for example, clothing, items of furniture, and basic commodities such as automobiles, etc. The sensation created by colour occurs, for example, in the case of an illuminated surface where the incident light is absorbed or reflected in such a way that the light reflected from the surface displays a specific spectral course which is perceived by the observer as colour. In order to manufacture colours and coloured surfaces in a reproducable way it is necessary to determine said spectral characteristic.

Knowledge of the spectral characteristics of colour is also important in order to accurately reproduce colour by photographic means, i.e. in printed matter or on film, etc., and in particular, in order to detect colour by electronic means, to tranfer the recorded data, and to accurately reproduce colour on the television screen and the visual display unit.

The spectral distribution of the light which, for example, is reflected from a coloured object, and which creates a specific colour sensation is referred to as the colour stimulus function $\phi(\lambda)$. On the one hand, the colour stimulus function is determined by the spectral distribution of the light $S(\lambda)$ which strikes the object, and on the other hand by the reflectance function $\sigma(\lambda)$ which depends on the wavelength characterizes the reflectivity. The colour stimulus function is expressed as follows $$\phi(\lambda) = \sigma(\lambda) \cdot S(\lambda)$$

This means that the colour stimulus function is the product of the spectral distribution of the light source, and the reflectance function.

If the light is not reflected from the object but passes through the object, the reflectance function is replaced with the transmission function $\tau(\lambda)$.

As the colour stimulus function is a function of the spectral distribution of the light which strikes the surface, this means that the colour sensation may change, if the spectral power distribution changes. Such differences can be observed, for example, when an object is first illuminated with natural light metamerism and then with artificial light.

It has been shown that the colour sensation which a colour elicits from a so-called standard observer can be described in terms of three variables, so-called primary variables. According to this theory the colour values, X, Y, and Z, of one colour, which are elicited by the colour stimulus function $\phi(\lambda)$ are determined by means of the following integrations:

$$X = k \int \lambda \sigma(\lambda) \bar{X}(\lambda) d\lambda$$

$$Y = k \int \lambda \sigma(\lambda) \bar{Y}(\lambda) d\lambda$$

$$Z = k \int \lambda \sigma(\lambda) \bar{Z}(\lambda) d\lambda$$

X, Y, and Z are the colour values, $\sigma(\lambda)$ is the colour stimulus function, whereas $\bar{x}$, $\bar{y}$, and $\bar{z}$ are the standard spectral value function as a function of $\lambda$. In 1931 a corresponding standard for colour values was established by the CIE (Commission Internationale de l'Eclairage) for the observation of small areas of colour, in particular, at a visual angle of of 2°. As a supplement to this system, a 10° system was introduced in 1964. In addition to these standards, there are also other colour standards which have been established by other standards organizations, which, as a rule, are based on the Young-Helmholtz three-colour theory.

There are a plurality of devices for measuring the colour characteristics of an object, the most important of which are briefly described in the following.

A typical passive colourimeter measures the radiation emitted by an object, as a result of its own radiation or reflection, by means of three photosensitive detectors. A filter is positioned in front of each of the detectors, by means of which the aforementioned spectral value functions $\bar{x}(\lambda)$, $\bar{y}(\lambda)$ and $\bar{z}(\lambda)$ are reproduced. The colour values X, Y, and Z can be calculated directly from the values measured by means of the sensors and then displayed. The disadvantage of this device, however, is that the filter functions must be extremely accurate reproductions of the spectral value functions, which is very costly. Moreover, these devices cannot record metameric effects.

If the device is used for measuring reflecting surfaces, the measured values are only valid if the sample is iluminated with a standard light, for example, such as those stipulated in the German industrial standard DIN5033.

Only the three colour values can be displayed with said colourimeter, the reflectance function as a function of $\lambda$, however, cannot be calculated.

The so-called spectrophotometer are another kind of colourimeter. This device is equipped, for example, with 16 or 32 narrow band filters along with a sensor, so that the intensity of the reflected light can be detected in a narrow wavelength range. This makes it possible to determine the reflectance function as a function of the wavelength over the respective wavelength ranges, from which the spectral distribution of this function can be plotted. During this process, however, a separate filter is required for each point on the spectral distribution curve which is used as a value. This also has the disadvantage that the construction of the device and particularly the manufacturing of the narrow band filter is very costly, which means that these devices are generally used in the laboratory only.

In the case of another type of spectrophotmeter the reflected light is split either by means of a prism, in which case the refraction is a function of the wavelength, or a grid, in which case the diffraction is also a function of the wavelength. These instruments, however, are very costly as regards their construction so that they too are used primarily in the laboratory.

The monochromator is another known colourimeter which permits the light of a specific wavelength only to strike the sample, which in turn makes it possible to detect the spectral distribution exactly. This device, however, is also very costly and like the spectrophotometer it is used preferably in the laboratory.

There have already been numerous endeavors to develop colourimeter which would be suitable for use outside the laboratory, i.e., in the manufacturing of goods and the like.

A device in accordance with the prior art portion of claim 1 has become known from publication DE 42 02 822 A1. This colourimeter is equipped with a cylindrical substrate, on one side of which a temperature sensor is mounted and on the other side of which light sources arranged in a circle are mounted and separated from a group of four photsensitive sensors by means of a cylindrical wall. The device is equipped further with a plurality of optical fibres, along which light can be guided from the light source to the area to be measured, where the light is reflected and guided to the sensors by way of the optical fibers.

Each of the light sources and sensors have different spectral characteristics. The light sources are supplied in turn with energy and the light reflected in each case is measured by means of the detectors.

A set of weighted integrations is then generated, where the number of integrations is the product of the number of light sources multiplied by the number of detectors. The weighting functions of the integrations are the product of the respective illumination weighting function and the respective sensor weighting function. From this set of weighted integration values, a set of weighted integration values is calculated by means of linear transformation, by the use of predetermined coefficients used for the transformation. It is thus possible to calculate standard colour values by using component parts whose spectral characteristics do not correspond to the characteristics for determining standard colour values. The apparatus has the disadvantage, however, that the spectral resolution is directly linked with the number of radiant sources and sensors. For example, 6 radiant sources are required in order to achieve a relatively low degree of resolution with 18 values, whose distance is furthermore not necessarily the same.

The present invention seeks to provide a device and a method for measuring and analysing spectral radiation, which can be manufactured easily and cost-effectively, and which will make it possible to provide measurements for radiation and analysis with high spectral resolution.

SUMMARY OF THE INVENTION

The invention provides a colourimeter which, on the one hand, is simply constructed, but on the other hand is designed in such a way that it is possible to detect the complete spectral distribution of a radiant source. In contrast to the known devices there is no need for exact and costly filters and no need for expensive grids.

The invention can be realized in different ways, the inventive principle being maintained in all embodiments.

In a first embodiment of the invention the device is designed as an active device. This means that the device is equipped with at least one radiant source in which electrical energy is converted to radiant energy. The reflected radiation of a sample to be measured, or, as the case may be, the radiation which passes through the sample is detected by means of sensor apparatus and is is analyzed by means of the control unit.

The assembly of said active device can be executed in different ways.

One of the first preferred embodiments is provided with a number of n radiant sources with different spectral characteristics, whose characteristics are selected in such a way that they overlap, at least partially, and that they are linearly independent of one another. A sensor which is sensitive to the whole relevant wavelength range of the radiation is provided for detecting the radiation which is either reflected from or passes through the object.

For each individual device a set of standard samples of known reflection characteristics are measured in the relevant wavelength range in order to calibrate the device. For example, if 8 radiant sources are used which are linearly independent of one another, 8 standard samples are used and their respective known reflection values in predetermined wavelength intervals are entered into the device, i.e. for 50 equidistant values in the relevant wavelength range between 380 and 780 nm. Measurement occurs in sequence, which means that for each individual light source the reflection intensities for all 8 standard samples are measured.

In this way, as explained in detail in the special description, eight calibration functions as a function of wavelength are generated. If the reflectivity or transmission of an unknown sample is to be measured, the eight measured values obtained for the eight different light sources are combined with said calibration functions, which gives the reflection/transmission of the sample.

It is thus possible to record the spectral characteristics of the sample in this manner without a monochromator and without complex spectral splitting of the light of an radiant source.

Should the resolution not be sufficient with, for example, 50 values, the accuracy can easily be increased by the use of 100 to 200 values.

In the second embodiment only one light source is used, which emits light with a predetermined characteristic in the entire relevant wavelength range. In this case a number of n sensors with different spectral characteristics are provided, whose wavelength ranges overlap, at least partially, and whose characteristics are linearly independent of one another.

A number of n standard samples are measured in this case as well and analysis is carried out in the same manner as described above with regard to the n different light sources.

In a third embodiment of the active device a number of n light sources with different spectral characteristics are provided, whose characteristics in the relevant wavelength range overlap, at least partially, and are linearly independent of one another. A number of m sensors with different spectral characteristics are also provided, whose characteristics likewise partially overlap and are linearly independent of one another.

In this case the standard samples p=nm are used for calibration and a linear set of equations is created in the same way and calibration functions are obtained, as in the case in the embodiments described above. Should there be no difference in the spectral sensor characteristics in a predetermined wavelength interval with respect to one of the light sources, the number of calibrating functions is reduced and, respectively, also the number of standard samples to be used.

A further preferred embodiment of the colourimeter is in the form of a passive device. In this device a radiant source is not provided, but rather a number of n sensors are provided having partially overlapping spectral characteristics which are lineally independent of one another. This device can be used to detect the spectral characteristics of active radiant sources such as the surrounding light, a specific light source, etc.

In said embodiment calibration takes place in a corresponding manner with the n active radiant sources, whose spectral characteristics in the relevant wavelength range are known.

For example, reflection standard samples of known reflection characteristics, which are illuminated with a separate light source of known spectral intensity distribution can be used as radiant sources. The colour stimulus function, which is detected by means of the sensors of the device, can be calculated from the product of the spectral characteristics of the light source and the spectral characteristics of the reflection standard sample. As in the embodiments described above, the calibration function is generated in turn from said known characteristics. On the basis of said function the spectral distribution of a radiant source is determined in the device from the measurements.

The measured and calculated values can be displayed in various ways with regard to all the embodiments described above.

The values are preferably to be displayed on a display unit which can either be built into the device or independent of the device in which case it can be linked up to the device by means of cables or the like.

The measured spectral distribution of the radiation can be represented on a display unit of this kind in the form of a conventional right-angled system of coordinates over the wavelength.

It is also possible to calculate colour values in accordance with one of the well-known colour standards from the spectral distribution. An outstanding feature of the device is that it is provided with a control unit which is equipped with several individual input switches by means of which several colour standards can be selected, which means that measurements can be analysed in different ways.

If this embodiment is developed further, the control unit can be designed in such a way that it is not only possible to provide the entire spectral distribution and standard colour values, but also measured values in such a way that the device simulates a particular type of device. This allows the user to directly compare the measured values of the device with the measured values of another type of device, even if the output of the other device is not carried out according to standard colour values.

In the following further advantages, features and applications of the present invention are described by way of example with reference to the accompanying drawings in which:

DESCRIPTION OF THE PREFERRED EMBODIMENTS

The invention will now be described with respect to the first embodiment whose construction is represented schematically in FIG. 1.

This embodiment is intended to be used for determining the reflectivity of the surface 1 to be examined.

The device comprises a light source 2 which in turn comprises a plurality of light emitting components L1 to L8 as well as sensor apparatus 3.

The light-emitting components L1 to L8 are LED's (light emitting diodes), the light sensor 3 can be selected from a group of photosensitive components, which include a photodiode, a phototransistor and a photoresistor, etc. It is important that the light sensor 3 be sensitive to the entire wavelength range, that is, to light in the range of between 380 and 780 nm.

The features of the LED's will be described in the following with respect to the way in which the embodiment functions.

The device is controlled entirely be means of a control unit 5 which is preferably provided with a microprocessor and the different signal inputs and signal outputs necessary for controlling the operation of the light sources L1 to L8 and for recording the measured values from the light sensor 3. The control unit is linked up to a storage device 6, in which a program for operating the control unit is stored, and in which the measured values are stored during the measuring process.

In this embodiment the control unit is also linked up to a display unit 8. The display unit is preferably an LCD (liquid crystal display) and is capable of representing numerals and graphic symbols.

The control unit is also linked up to an input device 9 which allows the user to enter instructions for the control unit. Said control unit may comprise several switches which are actuated by the user. However, it may also be provided with a full alphanumeric keyboard for entering numerals and letter.

The control unit 5 can be directly linked up to a computer, for example, to a mainframe or to a personal computer, instead of to the display unit 8 and the input device 9, or depending on the construction, to the storage device 6. In the case of a personal computer all the tasks performed by the control unit are controlled by means of the personal computer and the results are displayed on the display unit of the personal computer.

A printing device may also be provided for printing out letters, numerals and particularly graphic symbols.

In the following the way in which said embodiment functions and, in particular, the underlying mathematical analysis will now be explained with reference to FIGS. 2 and 5:

The device comprises 8 LED's whose respective spectral distributions in the wavelength interval between 380 and 780 nm are different. In this case, different means that the spectral courses, as represented in FIG. 2, are linearly independent of one another. The desired linear independence can be achieved by the selection of a corresponding number of LED's with different spectral characteristics, or by providing the LED's with a filter which gives a spectral distribution to the light emitted from the light source as a whole, which is linearly independent of the distribution of the other LED's.

The spectral characteristics of the LED's must be further selected in such a way that their ranges overlap at least in part, thus ensuring that the illumination of a sample will be carried out in the entire relevant wavelength range.

Figure 2:
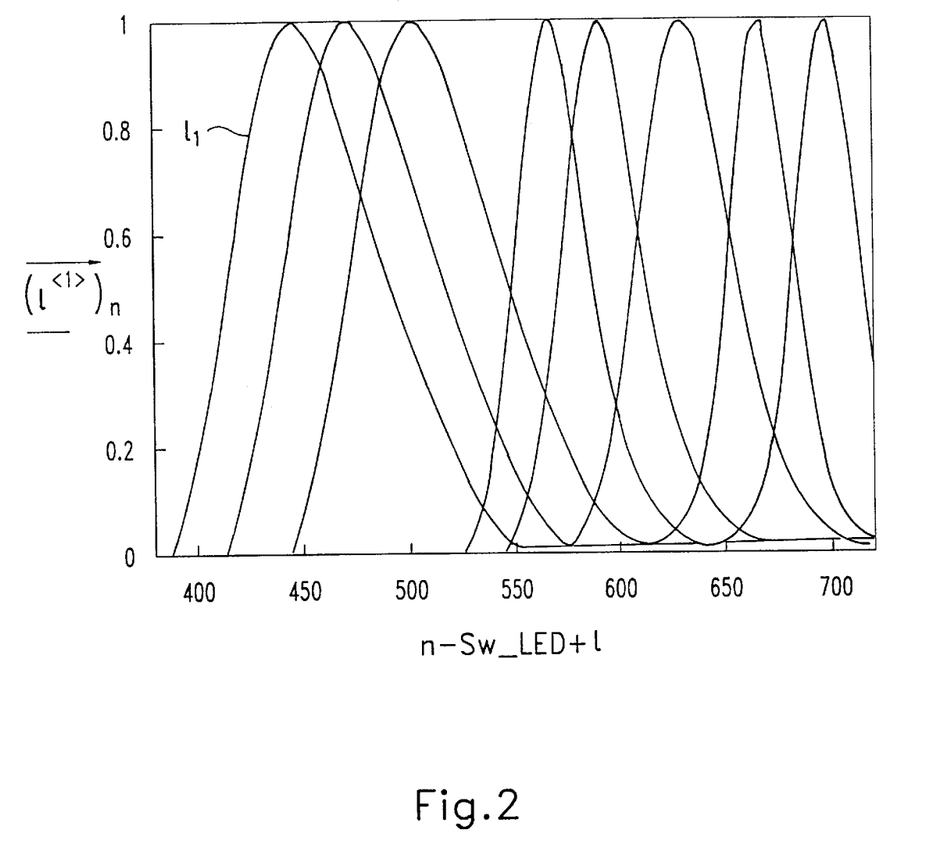
FIG. 2 is a diagram which shows the spectral intensity distribution of eight different LED'S, where the intensity is represented by the axis of ordinate and the wavelength by the axis of abscissa.

FIG. 2 shows an example of a spectral wavelength distribution of 8 LED's, as required in accordance with the invention. The intensity of the LED's is displayed on the axis of ordinate, which is standardized to a value 1, whereas the wavelength range between 380 and 780 nm is displayed on the axis of abscissa.

The calibration, which is decisive for the operation of the device, will be described in detail in the following.

A number of standard samples having known reflectance spectra are used in order to calibrate the device. The spectral distributions of the individual standard samples are again likewise linearly independent of one another.

Figure 3:
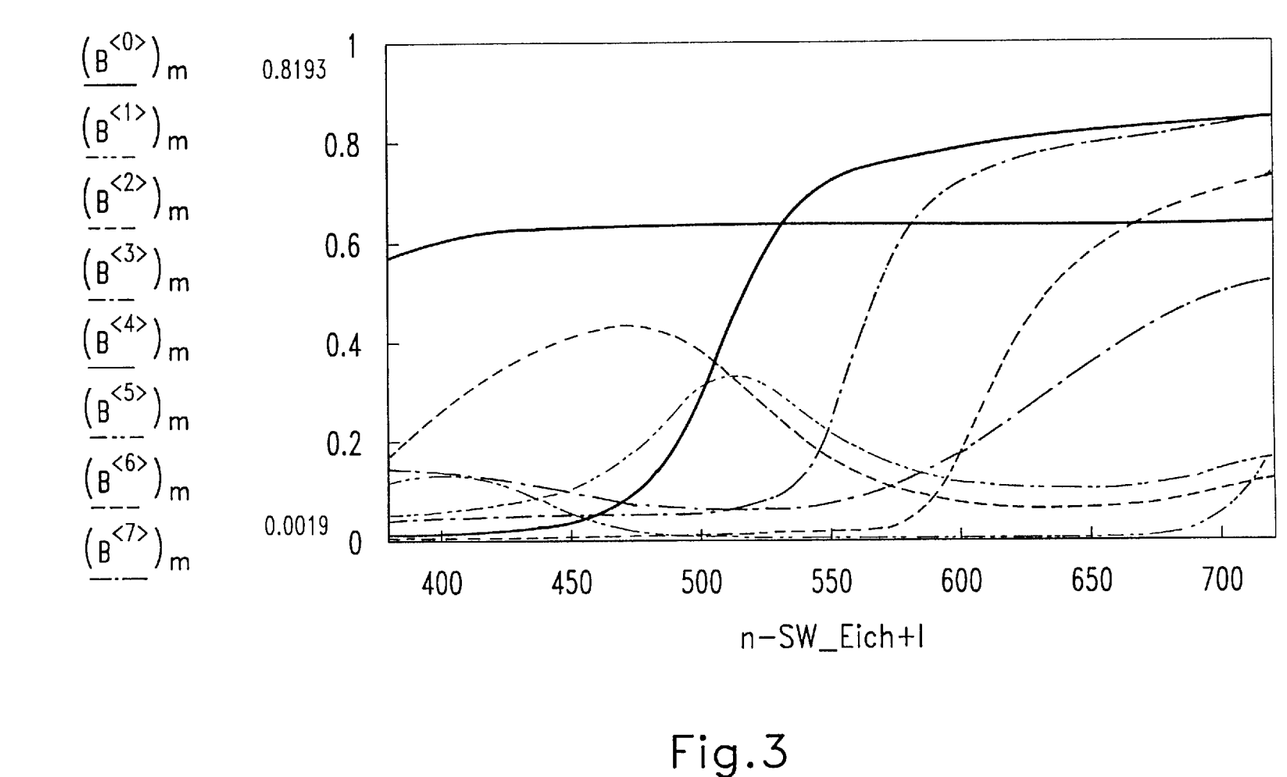
FIG. 3 shows the reflectance spectra of eight standard samples; the remission capacity is plotted on the axis of ordinate and the wavelength on the axis of abscissa.

The spectral intensity distribution of 8 selected standard samples are shown as examples in FIG. 3. In FIG. 3, the dimensionless value for the reflectance capacity is display on the axis of ordinate, whereas the relevant wavelength range of between 380 and 780 nm is plotted on the axis of abscissa.

In order to calibrate the device, each standard sample is illuminated in turn by means of the individual light sources L1 to L8 and the intensity of the reflected light is measured by means of the sensor 3. The measured values are recorded by the control unit 5 and are stored in the storage unit 6 of the device. If, as in the present case, 8 light sources are used, correspondingly, 8 standard samples will be used for calibration.

In order to analyse the calibration the following mathematical operation is used:

The reflectance for each of the standard samples over the entire wavelength range is known. If only a section of said wavelength range is to be observed, namely, the interval $\Delta\lambda$, the following equation for the relationship between the measured sensor signals and the actual reflectance in said interval is created:

$$I_{\Delta\lambda} = K_1 L_1 + K_2 L_2 + \ldots + K_n L \quad\quad 1.1$$

where $I_{\Delta\lambda}$ is the reflectance of the standard sample in the interval $\Delta\lambda$, $L_i$ the measured remitted intensity of the light source i, and $k_{i,\lambda n}$ coefficients for the interval $\Delta\lambda$ An equation is thus produced with n unknown coefficients $K_1$ to $K_n$, n being the number of linearly independent light sources.

As explained above, standard samples m are used for the calibration, the number of m being equal to the number of linearly independent light sources n.

If the reflectance is observed in the given interval $\Delta\lambda$ for each of the standard samples m, the following set of equations is produced:

$$
\begin{aligned}
I_{1\lambda} &= K_{1\lambda}L_{11} + K_{2\lambda}L_{21} + \ldots + K_{n\lambda}L_{n1} \\
I_{2\lambda} &= K_{1\lambda}L_{12} + K_{2\lambda}L_{22} + \ldots + K_{n\lambda}L_{n2} \\
&\vdots \\
I_{n\lambda} &= K_{1\lambda}L_{1n} + K_{2\lambda}L_{2n} + \ldots + K_{n\lambda}L_{nm}
\end{aligned}
\quad 1.2
$$

where $I_{k\lambda}$=reflectance of the standard sample k at position $\lambda$ $L_{i,k}$=measured intensity at light source i on standard sample k, $k_{i,\lambda}$=coefficient of light source i at position $\lambda$.

This is a linear set of equations, in which the values $I_1(\lambda)$ to $I_n(\lambda)$ are known because standard samples with known reflectivity in the range $\Delta\lambda$ have been measured, and in which, further, the value L is known as the result of the measuring process, and wherein those values can be functions in which other parameters e.g. the temperature, can be considered. The coefficients $K_1$ to $K_n$ are unknown in this equation.

As the respective characteristics of the LED's and the standard samples are linearly independent of one another, the solution to this set of equations includes in any case a non-trivial solution. The solution which is reached when the coefficient matrix of the set of equations is inverted and multiplied by the known reflectance values of the standard samples, thus producing coefficients K1 to Kn, as expressed below in equation 1.3.

$$
\begin{pmatrix}
L_{11} & L_{21} & \ldots & L_{n1} \\
L_{12} & L_{22} & \ldots & L_{n2} \\
\vdots & \vdots & & \vdots \\
L_{1n} & L_{2n} & \ldots & L_{nm}
\end{pmatrix}^{-1}
\cdot
\begin{pmatrix}
I_{1\lambda} \\
I_{2\lambda} \\
\vdots \\
I_{n\lambda}
\end{pmatrix}
=
\begin{pmatrix}
k_1 \\
k_2 \\
\vdots \\
k_n
\end{pmatrix}
\quad 1.3
$$

This set of equations refers to a very specific predetermined wavelength interval $\Delta\lambda$. If the relevant wavelength range is subdivided into a number of x equal intervals $\Delta\lambda$, correspondingly, x linear sets of equations of the kind described in equation 1.3 are created.

If the interval $\Delta\lambda$ is permitted to decrease, the number of x is thus increased in the relevant wavelength range. As a result it then finally becomes possible to carry out the transition to the limit value 1.4.

$$\lim_{\Delta\lambda \to 0} \Delta\lambda \quad\quad 1.4$$

The discrete reflectance values $I_{k\Delta\lambda}$ for a predetermined interval are no longer found on the left side of the set of equations 1.2, but rather the continuous reflectance spectra $I_{k(\lambda)}$ of the standard samples.

On the right side of equation 1.2 the discrete coefficients $k_{i,\Delta\lambda}$ become the function of $\lambda$ and after transposition the following solution to the set of equations is generated:

$$\begin{pmatrix} L_{11} & L_{21} & \ldots & L_{n1} \\ L_{12} & L_{22} & \ldots & L_{n2} \\ . & . & . & . \\ . & . & . & . \\ . & . & . & . \\ L_{1n} & L_{2n} & \ldots & L_{nk} \end{pmatrix}^{-1} \cdot \begin{pmatrix} I_1(\lambda) \\ I_2(\lambda) \\ . \\ . \\ . \\ I_n(\lambda) \end{pmatrix} = \begin{pmatrix} k_1(\lambda) \\ k_2(\lambda) \\ . \\ . \\ . \\ k_n(\lambda) \end{pmatrix} \quad 1.5$$

where $L_{i,k}$=measured sensor signal when operating light source i is on standard sample k, $I_{k(\lambda)}$=reflectance spectrum of standard sample k, $k_{i(\lambda)}$=calibration functions for the individual light sources $k_1(\lambda)$ to $k_n(\lambda)$ are now calibration functions which indicate how the incident light striking the sample, which originates from the light sources L1 to L8, is composed in proportion to the light from the individual light sources.

When the method is implemented using a device which operates with a conventional digital microprocessor, the transition to the limit value $\Delta\lambda \to 0$ is not carried out. Instead, a correspondingly large number of x values, i.e. 50 or 100 values, are selected depending on the desired level of resolution. Instead of the continuous calibration functions, functions which are identified by means of discrete values are produced. If the chosen number of x values is large enough, however, the continous calibration function course will be generated with no difficulty from the discrete function because the reflection characteristics contain no discontinuities.

The discrete function values of the calibration functions are permanently stored in the microprocessor.

Figure 1:
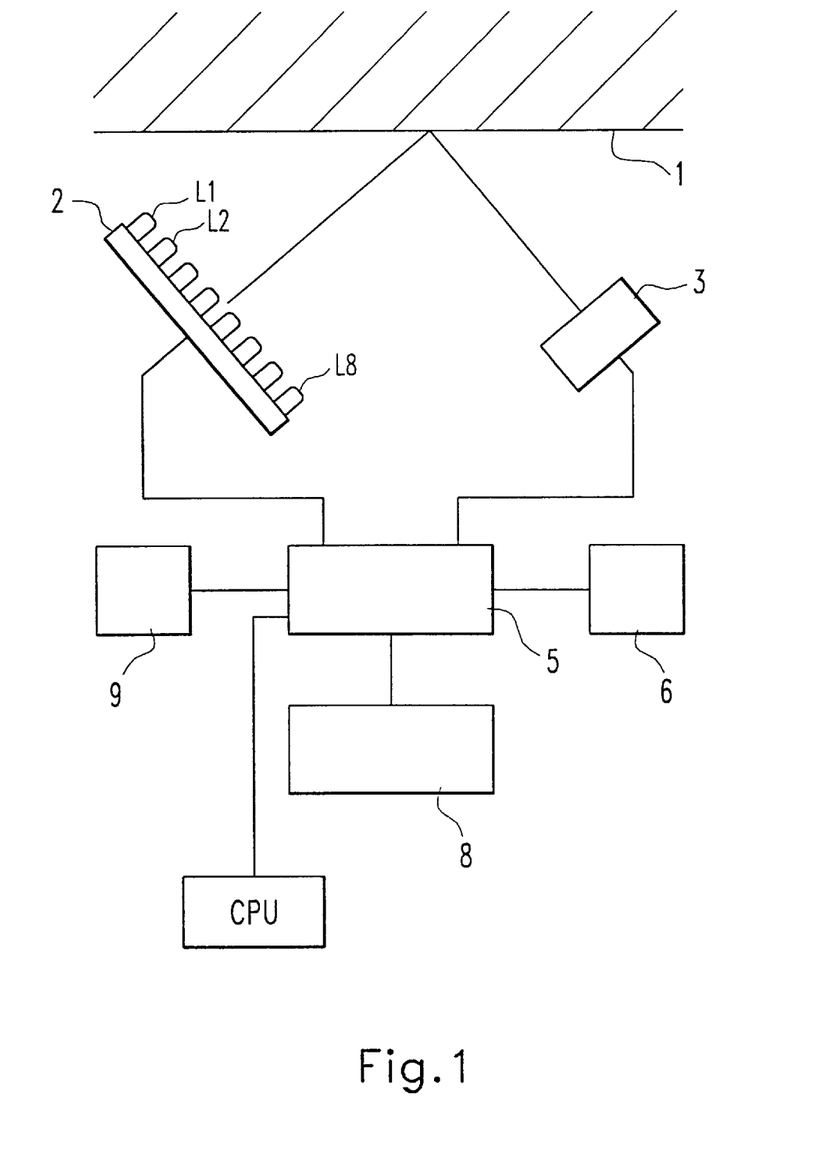
FIG. 1 is a schematic representation of a first embodiment of the device in accordance with the invention.

The actual measuring process will now be carried out as follows:

The surface to be measured, as shown in FIG. 1, is illuminated in turn by means of the LED's L1 to L8 and the measured values are stored. From these values a measuring vector M along with individual values M1 to Mn are produced. M has as many components as there are linearly independent light sources L1 to L8. If a photodiode is used as sensor 3, which is preferable, the individual components of the measuring vector, M1 to M8, are voltage values, which are measured in volts and then stored. In this case even the discrete individual values of the calibration functions are stored directly in volts.

The measuring vector is multiplied by the discrete values of the calibration functions. The following equation is used:

$$\text{Result}_{o \leq r \leq x} = \sum_{n=0}^{7} \overrightarrow{\text{Mess}} \cdot K_{n,r} \quad 1.6$$

Result refers to the intensity at a specific value T. Mess refers to the measuring vector and $K_{n,r}$ to the discrete calibration values for the LED's with the number n and the value r.

The result is thus the spectral power distribution over the relevant wavelength range for x values.

The method of calibration and the measuring process will now be explained by way of an example for measuring.

The reflectance values of 8 different standard samples were measured by means of 8 different LED's which are components of the device in accordance with the invention, whose construction corresponds to the construction shown in FIG. 1. A matrix of measured values L were generated from said values, which are displayed in Table 1. The rows correspond to the individual standard samples and the columns to the LED's. The values of the matrix are the voltage values which were directly detected by the light senor 3 expression in volts.

The reflectance values for the standard samples are predetermined and given intervals of 10 nm, ranging between 380 and 720 nm and are standardized to a dimensionless value of 1, which corresponds to a reflectance value of 100%. The resulting matrix is expressed as follows:

$$I = \begin{pmatrix} \text{white}(\lambda = 380) & \text{white}(\lambda = 390) & \ldots & \text{white}(\lambda = 720) \\ \text{pink}(\lambda = 380) & \text{pink}(\lambda = 390) & \ldots & \text{pink}(\lambda = 720) \\ . & . & . & \\ . & . & . & \\ . & . & . & \\ \text{blue}(\lambda = 380) & \ldots & & \text{blue}(\lambda = 720) \end{pmatrix}$$

The individual lines correspond in turn to the individual standard samples, i.e. the first row contains the values (which are not reproduced in the table itself) for one standard sample with the colour white, the second row contains the values for a standard sample with the colour pink, and the last row represents the values for a standard sample with the colour blue. As a result of the division into intervals of 10 nm, for the sake of simplicity, there are 35 values in the range of 380 to 720 nm. This means that each row of matrix I comprises 35 individual function values altogether.

Figure 4:
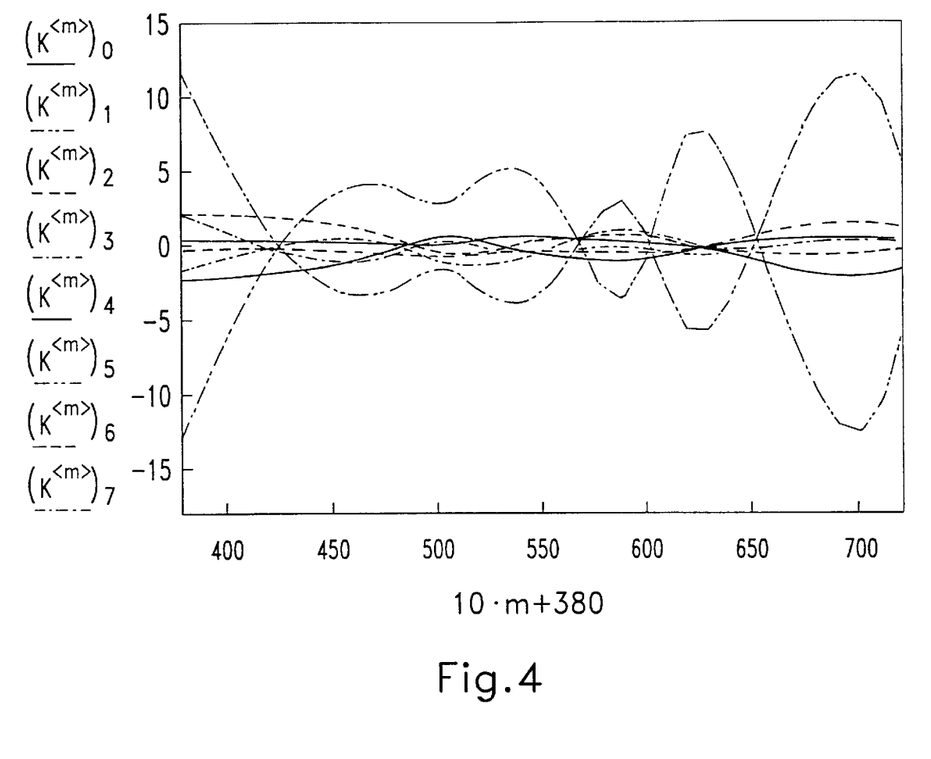
FIG. 4 shows the calibration functions with respect to example of calibration for the embodiment in accordance with FIG. 1.

The matrix L is inverted and multiplied by the values of I, which produces the calibration functions shown in FIG. 4.

The following measuring vector was created for the individual LED'S when an unknown sample was measured:

$\overrightarrow{\text{MESS}}$=1.26, 1.173, 1.32, 1.11, 1.19, 1.095, 1.295, 1.115

These values are likewise expressed in volts.

The measuring vector M and the calibration functions are multiplied. As there are 35 discrete values, the calibration values for each value are multiplied by the measuring vector, and the individual values are added, as shown in equation 1.6.

Figure 5:
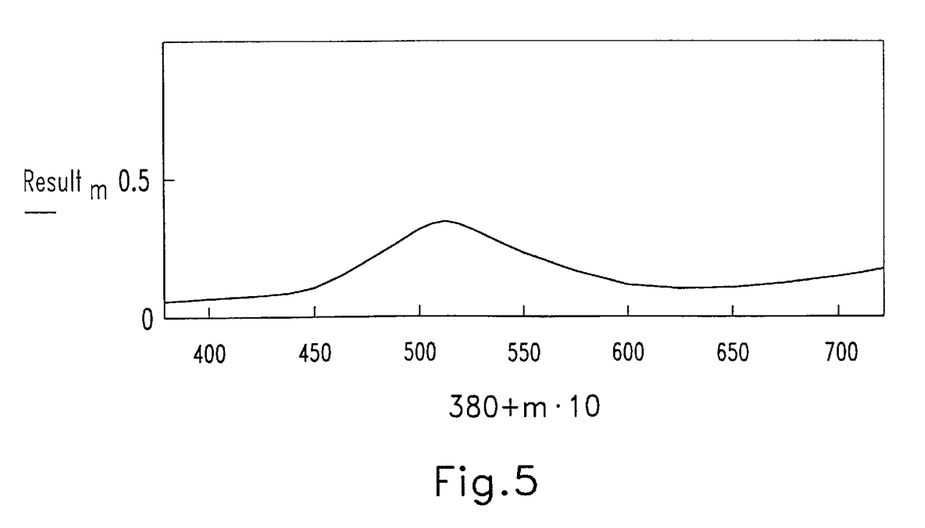
FIG. 5 is an example of a measurement used for calculating the example of an embodiment in accordance with FIG. 1 is being calculated.

The spectral course of the sample can thus be derived, as shown in FIG. 5. In this sample, the reflectivity is plotted on the axis of ordinate, whereas the wavelength range is plotted on the axis of abscissa. The skilled person will recognize that a green sample has been measured from the spectral distribution.

As demonstrated by the example, it is possible by means of the method in accordance with the invention to obtain the spectral power distribution over the entire range of visible light by using a relatively small number of only 8 LED's. Should the user wish to obtain further information, the colour values according to CIE, ASTM or DIN can be calculated from the spectral distribution in accordance with the known relationships of colourimetry.

A further embodiment of the invention will now be described with reference to FIG. 6.

In contrast to the example in accordance with FIG. 1, in this example provision is made for only one radiant source 21, which emits light to the entire relevant wavelength range. The light of the radiant source 21 is reflected from the sample 20 and strikes the sensors S1 to S8 whose respective wavelength characteristics overlap, at least partially, and are linearly independent of one another.

The linear independence can be achieved by the use of a corresponding number of different kinds of sensors or by providing the sensors with filters which produce the desired different spectral distribution.

The remaining components of the control unit 5, storage device 6 and display unit 8, etc. are the same as those used in the example according to FIG. 1.

The way in which this embodiment functions is as follows:

The light source 21 is actuated once and the signals emitted by sensors S1 to S8 are recorded by the control unit 5 and stored in storage means 6.

A set of equations is created in the same way as the equations 1.1 and 1.5 as explained above. In contrast to the aforementioned equations, however, in this case L1 is not the measured remitted intensity of the light source I, but rather the remitting intensity measured by means of the sensor I. Likewise, $K_{I,\lambda}$ is the coefficient of the sensor I at position $\lambda$ and the calibration function $K_{I(\lambda)}$ form the calibration functions for the individual sensors.

Incidentally, the same applies to the mathematical analysis and to the calculation of the spectral distribution from the measured values as explained above with reference to the example of the embodiment in accordance with FIG. 1.

A further example of an embodiment of the invention will now be described with reference to FIG. 7.

This embodiment is provided with three light sources L1, L2 and L3, which as a whole are referred to as radiant sources 31. The light from said light sources which is reflected from the sample 30 is detected by means of receiving device 32, which is provided with three sensors S1, S2 and S3.

The respective spectral characteristics of the light sources L1, L2 and L3 overlap, at least in part, and are linearly independent of one another. The same applies to the sensors S1, S2 and S3.

The remaining components of the device correspond to the components as they were described with reference to FIGS. 1 and 6.

Figure 6:
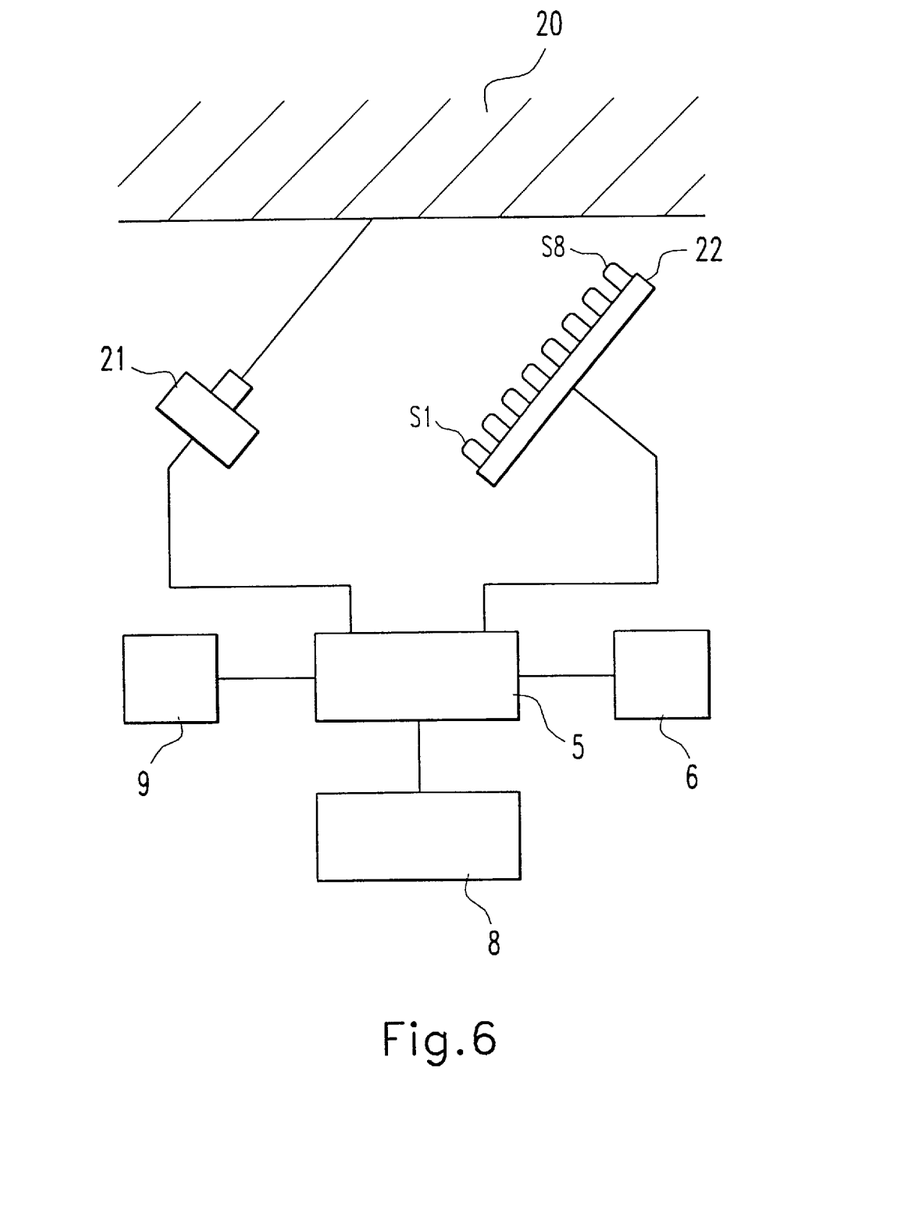
FIG. 6 is a schematic representation of further embodiment of the invention.

The way in which this embodiment functions is as follows:

The calibration is carried out in the same way as decribed with reference to FIGS. 1 and 6. In this embodiment, however, 9 standard samples in all are required and each standard sample is illuminated in turn by means of the light sources L1, L2 and L3. The respective values which were measured by means of sensors S1 to S3 are stored in the storage device. Calibration functions are then generated in a similar manner to that described above, starting from the following equation:

$$I_{\Delta\lambda} = \sum_{i=1}^{i=3} \sum_{j=1}^{j=3} K_{i,j} \cdot L_{i,j} \qquad 1.1'$$

where

I=reflectance of the standard samples in interval $\Delta\lambda$ $K_{I,J}$=coefficient for the respective $\Delta\lambda$ for the light source I and the sensor J $L_{I,J}$=the remitted of light source I measured by sensor J n=I.J unknown coefficients $K_{I,J}$, are thus produced, which means that in the case of the present embodiment, which has three light sources and three sensors, that there are nine unknown coefficients altogether. In the case of nine standard samples a set of equations is produced which is again similar to that described in equation 1.2, and which comprises nine equations having nine unknown coefficients. As described above, this set of equations can be solved, thus producing nine calibration functions. The spectral distribution is then calculated from these calibration functions in the same way as described with respect to the embodiment according to FIG. 1.

Figure 8:
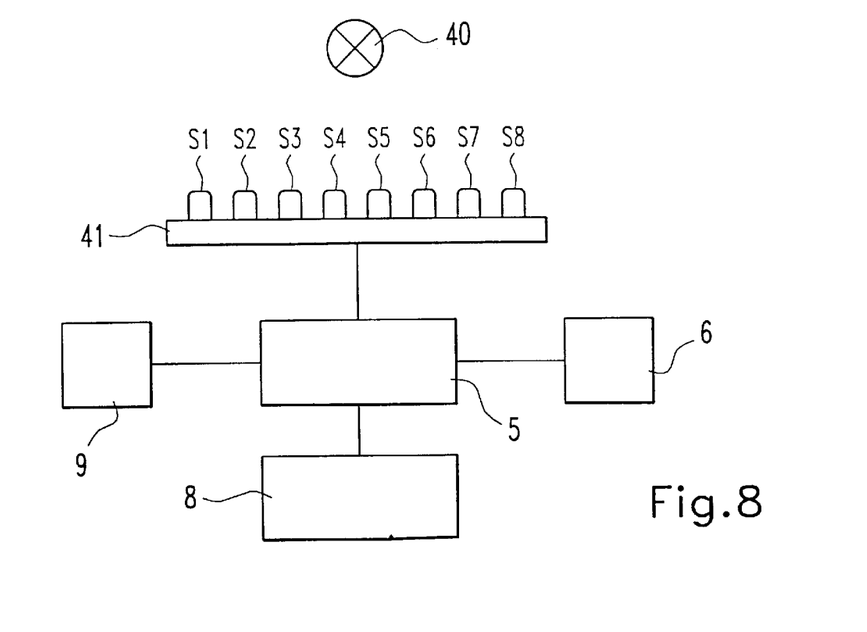
FIG. 8 is a schematic representation of a further embodiment of the invention.

A further example of an embodiment will now be described with reference to FIG. 8.

This embodiment is intended for the measurement of actively irradiating radiant sources, in other words, no device is provided for illuminating a sample by means of a light source.

The radiant source as a whole is identified as 40 and a sensor apparatus 41 with 8 sensors S1 to S8 is also provided in oder to detect the radiation emitted from the radiant source 40. The sensors S1 to S8 overlap, at least in part, in the relevant range and display spectral characteristics which are linearly independent of one another.

The remaining components of the device correspond to the components which were described with reference to the other examples of embodiments.

The way in which this device functions is as follows:

For calibrating the device, a construction is used which corresponds to the construction used for the device according to FIG. 6. This means that a light source of known spectral distribution is used, with which a number of standard samples are illuminated which correspond to the number of the sensor apparatus 41. A calibration function is generated from the recorded measured values which are stored in the storage device 6, as described above. A corresponding number of light sources with known spectral characteristics may also be used instead of the standard samples.

In the measuring process, the light of the radiant source to be measured is recorded. The radiant source may be an actively irradiating source such as a lamp, an LED or the like, or it may also be a passive radiant source such as a surface which is illuminated by means of artificial light or daylight. The radiation emitted from the radiant source is detected by means of sensors S1 to S8 and the measured values are stored in the storage device 6. The spectral distribution of the radiant source is then calculated by means of the stored calibration functions, as mentioned above.

A further embodiment of the invention will now be described with reference to FIGS. 9 and 10. This embodiment of the description shows the actual construction of a colour measuring head for holding radiant sources and sensors.

The measuring head, which is identified as a whole as 100, comprises an axially symmetrical bell-shaped measuring head, in which the the radiant sources and sensors are fitted. The measuring head comprises a cylindrical section 100a which is joined to a section 100b which is linearly tapered. A circular section 100c is joined to the tapered section 100b. The tapered section 100b is at an angle of $\alpha$ to the axis of the axially symmetrical bell, for example at an angle of 45°. In said tapered section there are 24 bores 101 altogether arranged equidistantly with the same anglular distance in relation to the axis of radial symmetry of the bell-shaped measuring head and on the same plane as said axis. 24 LED's 110 or, as the case may be, 24 sensors are positioned in the bores 101 or 24 sensor respectively, as will be explained later on.

In the circular section 100c of the bell, there is a bore 104 which is positioned concentrically to the axis of radial symmetry and in which a measuring cylinder 105 is attached by means of an adhesive or the like. A predetermined length of the measuring cylinder projects into the bell and bears a lens 108 which faces the open end 100d of the bell. At the other end of the cylinder facing away from the lens, a filter 102 is provided behind which a sensor 106 is attached.

The way in which this embodiment functions is as follows: The colour measuring head is intended to be used in a construction as described with reference to FIG. 1. The 24 LED's 101 thus correspond to the LED's L1 to L8 shown in FIG. 1.

The 24 LED's are arranged in groups comprising three LED's, which are arranged at an angular distance of 120° relative to one another and which emit identical light. The colour measuring head thus comprises 8 groups of different LED's. The spectral distribution of the 8 kinds of LED's overlap with one another, at least in part, in the relevant wavelength range and are linearly independent of one another. The use of groups of 3 LED's arranged at the circumference has the advantage that should shadows perhaps form as a result of textured surfaces, the measured values will not be distorted.

The sensor 106 corresponds to sensor 3 in FIG. 1 and can measure the intensity of the light in the entire relevant wavelength range.

In order to measure, the colour measuring head with the bell 100 is placed on top of the surface to be measured, preferably in such a way that no undesirable light can enter the bell. The respective groups of three LED's 101 are activated in turn and emit their light in the direction of the area to be measured which is located on the sample generally along the extension of the axis of radial symmetry 103 of the bell. The light reflected from the area to be measured is detected by means of sensor 106 and stored in the storage device 6 of the device. As soon as all the groups of LED's have been activated and the measured values have been recorded and stored in the storage device 6, the analysis, as described above with respect to the embodiment in accordance with FIG. 1, begins.

Figure 9:
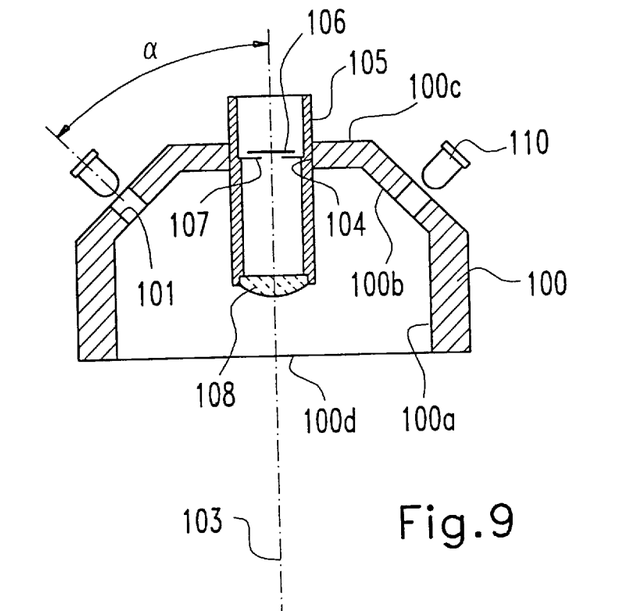
FIG. 9 is a closeup view of a measuring device a colour measuring head, in particular, for placing on top of the surface to be measured, and which is drawn in section and FIG. 10 a view of an embodiment of the invention in accordance with FIG. 9.

As can be seen in FIG. 9, the angle design of the tapered section of the bell ensures that the light emitted from the LED'S strike the surface to be measured at a 45° angle. If the reflection were to correspond exactly to Fresnel's law of reflection, according to which the angle of incidence is equal to the angle of reflection, this would mean that the light emitted from the LED's would not be reflected to the sensor but rather from the respective opposite walls. Thus it is ensured that the sensor does not detect reflection according to Fresnel, but rather the diffuse reflection of the surface to be measured, which is decisive for the colour sensation.

In order to calibrate the device, the measuring head is placed on top of standard samples of known reflectivity and the measured values for calibration are brought into play, as described with reference to FIG. 1.

Figure 10:
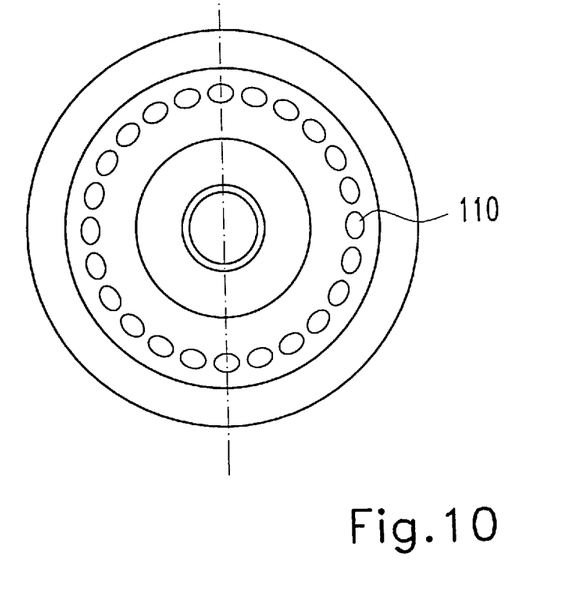

In the case of the embodiment represented in FIGS. 9 and 10, 24 LED's are used altogether which are connected up in respective groups of three. It is possible to use a greater or smaller number of LED's and to arrange the groups in a different manner.

Figure 7:
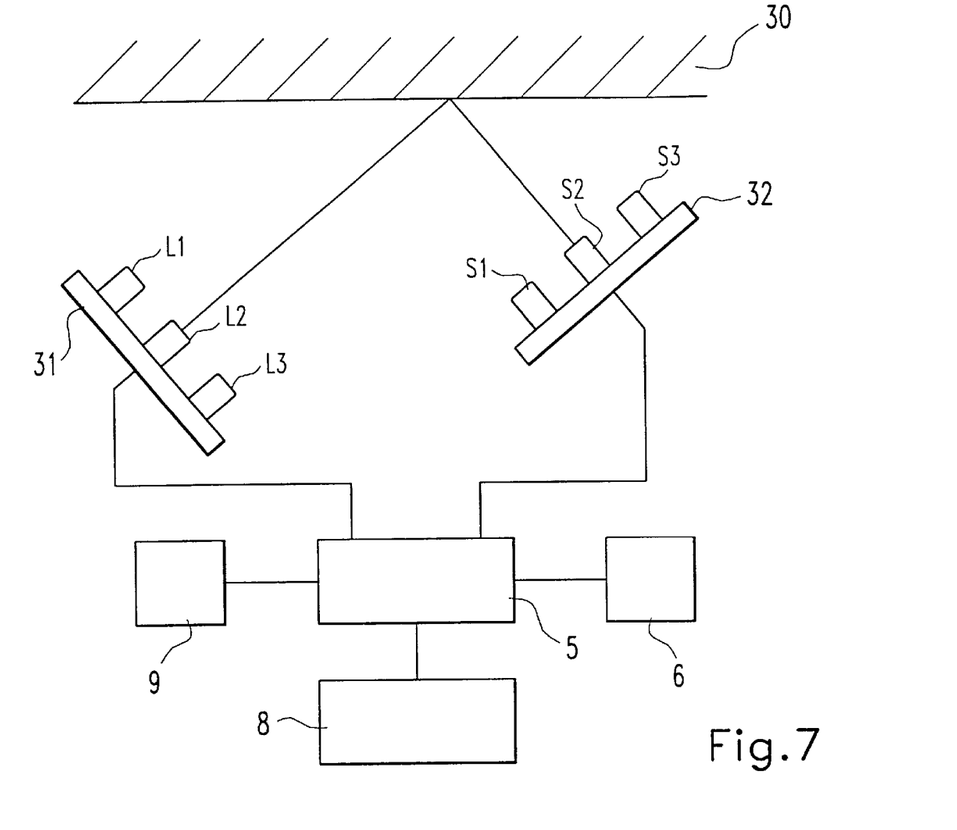
FIG. 7 is a schematic representation of a further embodiment of the invention.

A variation of the embodiment (not shown) according to FIGS. 9 and 10 corresponds to the embodiment according to FIG. 7.

In this embodiment a colour measuring head, as shown in FIG. 9, is used. Instead of the sensor 106, however, a radiant source is used in the cylinder, which covers the entire relevant wavelength range, and sensors, instead of the LED's 110, are positioned in the bores 101. If the embodiment is constructed analogously to the embodiment according to FIG. 7, the device be provided with 8 bores 101 altogether and 8 sensors will be used altogether the spectral characteristics partially overlap and which are linearly independent of one another.

For the reason of completeness it is described in the following how the measured reflected light intensities on a surface with known spectral characteristic can be determined theoretically:

$$L_{i,j}(U) = \int_{-\infty}^{+\infty} K_j(\lambda) \cdot \phi_j(\lambda, U) \cdot \sigma(\lambda)$$

where $L_{i,j}(U)$=reflected light intensity (measured value), $K_i(\lambda)$=reflectance functions of the standard sample i, $\phi_j(\lambda,U)$=spectral characteristic of the light source j depending on the temperature dependent measured value U, $\sigma_j(\lambda)$=characteristic of the sensors These integrals can be represented as a power progression:

$$L_{i,j}(U) = \alpha_{0,i,j} + \alpha_{1,i,j} \cdot (U - U_{0,i,j}) + \alpha_{2,i,j} \cdot (U - U_{0,i,j})^2 + \ldots$$

$$L_{i,j}(U) = \sum_{n=0}^{\infty} \alpha_{n,i,j} \cdot (U - U_{0,i,j})^n$$

where:

$\alpha_{n,i,j}$=development coefficient of the order n for the measured value of the standard sample i and the light source j $U_{0,i,j}$=temperature dependent measured value (e. g. anode voltage) with reference temperature U=temperature dependent measured value with any temperature The coefficients are of the power progression can be determined with the following system of equations:

$$S(U_{0,i,j}) = \alpha_{0,i,j}$$
$$S(U_{1,i,j}) = \alpha_{0,i,j} + \alpha_{1,i,j} \cdot (U_{1,i,j} - U_{0,i,j}) + \alpha_{2,i,j} \cdot (U_{1,i,j} - U_{0,i,j})^2 + \ldots + \alpha_{2,i,j} \cdot U_{1,i,j} - U_{0,i,j})^n$$
$$\vdots = \vdots + \vdots + \vdots + \ldots + \vdots$$
$$S(U_{n,i,j}) = \alpha_{0,i,j} + \alpha_{1,i,j} \cdot (U_{n,i,j} - U_{0,i,j}) + \alpha_{2,i,j} \cdot (U_{n,i,j} - U_{0,i,j})^2 + \ldots + \alpha_{2,i,j} \cdot U_{n,i,j} - U_{0,i,j})^n$$

where:

$S(U_{k,i,j})$=measured value of the sensors with temperature dependent measured value $U_{k,i,j}$ of the light source $U_{k,i,j}$=temperature dependent measured values with temperature k and standard sample i and light source j k=0. . . n=order of the power progression $\alpha_{k,i,j}$=coefficient of the order k for standard sample i and light source j In this system of equations, the term $U_{k,i,j}$ can be combined in an i*j matrix:

$$\underline{U}^{i,j} := U_{l,k}^{i,j} = (U_{l,l,j} - U_{0,i,j})^k$$

where:

l=0. . . n index of the measured value by different temperatures k=0. . . n exponent of the power progression i=index for the standard sample, j=index for the light source Consequently, the above identified system of equations can be represented in the following form:

$$\overrightarrow{S(U_{i,j})} = \underline{\underline{U^{i,j}}} \cdot \overrightarrow{\alpha_{i,j}}$$

and it can be resolved to $\alpha_{i,j}$:

$$\overrightarrow{\alpha_{i,j}} = \underline{\underline{(U^{i,j})}}^{-1} \cdot \overrightarrow{S(U_{i,j})}$$

Consequently, the spectrum of reflectance of a sample to be measured can be determined in the following way:

Recording and storage of m sensor signals and related light source parameters (e.g. through voltage of the single LEDs) for a sample:

$\vec{P}$ (measured values of the sensors) and $\vec{V}$ (light source parameters)

Calculation of the calibrating functions (those values of the calibration functions are calculated, which would be obtained if the standard samples would be measured by the actual light source temperature):

$$E(\lambda) = \vec{P} \cdot \overrightarrow{K(\lambda)}$$

where $E(\lambda)$ = resulting function, P = measured value vector, $\overrightarrow{K(\lambda)}$ = calibrating functions where:

$$\overrightarrow{K(\lambda)} = \underline{\underline{(L(V))}}^{-1} \cdot \overrightarrow{I(\lambda)}$$

where $\underline{\underline{(L(V))}}^{-1}$ = inverse of the corrected standard sample matrix, $\overrightarrow{I(\lambda)}$ = reflectance spectrums of the standard samples, and:

$$L_{i,j}(V) = \vec{M}_{i,j} \cdot \vec{\alpha}_{i,j}$$

$$\vec{M}_{i,j} := M_{i,j}{}^k = (V_j - U_{0,i,j})^k$$

where $V_j$ = actual measured value of the temperature dependent parameters of the light source j, $U_{0,i,d}$ = temperature dependent measured value (e.g. anode voltage) with reference temperature.

Replacement of $\alpha$ results in:

$$L_{i,j}(V) = \overrightarrow{M_{i,j}} \cdot \underline{\underline{U}}^{-1} \cdot \overrightarrow{S(U_{i,j})}$$

and consequently, the resulting function can be calculated according to the following form:

$$\rightarrow E(\lambda) = \vec{P} \cdot (\overrightarrow{M_{i,j}} \cdot \underline{\underline{U}}^{-1} \cdot \overrightarrow{S(U_{i,j})})^{-1} \cdot \overrightarrow{I(\lambda)}$$

As the above embodiments demonstrate, the present invention makes it possible to create a device for measuring and analyzing spectral radiation, thus making it possible to record the spectral distribution of radiation by using a relatively small number of radiant sources or, as the case may be, sensors. As a result of its simple construction, the device can be designed to be relatively small in size and easy to handle, so that it can be used not only in the laboratory but that it can be implemented directly in industry in order to continuously monitor colour quality.

I claim:

1. Apparatus for measuring and analysing spectral radiation within a predetermined wavelength range and particularly for detecting the characteristics of colors, comprising:

a number of N1 radiant sources which emit radiation which is distributed spectrally over a wavelength range which lies, at least partially, within said predetermined wavelength range, where the spectral characteristics of said individual radiant sources differ from one another and N1 is greater than or equal to 1, sensor apparatus which detects radiation within said predetermined wavelength range and generates an electrical signal which is representative of the intensity of the detected radiation, a control unit which controls the radiation of said apparatus and which causes the radiant sources to be actuated in predetermined combinations at successive intervals of time, a storage device, in which the values detected by means of the sensor apparatus for the respective combinations of radiant sources are recorded and stored, the control unit calculates values from said stored values for identifying the spectral characteristics of the radiant sources, characterized in that the radiant sources are selected in such a way that their spectral characteristics overlap with said predetermined wavelength range, that the spectral characteristics of the light sources furthermore are such that the characteristics of at least N2 of said light sources are linearly independent of one another, that said sensor apparatus comprises a number of M1 sensors whose spectral characteristics in the predetermined wavelength range overlap in such a way that the entire predetermined wavelength range is covered, where M1 is greater than or equal to 1;

that the spectral characteristics of the sensors are furthermore such that the characteristics of at least M2 of said radiant sources are linearly independent of one another, that the product P=N2*M2 derived from the multiplication of the values for N2 and M2 is greater than 1;

that in said storage device a number of P calibration functions are stored which span the predetermined wavelength range at least in part, and which define the relationship between the spectral intensity distribution of P standard samples, which is measured by means of the individual device, and their known reflectance spectra, the spectral characteristics of the reflectance spectra being linearly independent of one another and overlapping, at least partially, in such a way that the entire wavelength range is recorded and that by combining said calibration functions with the measured values for the radiation to be measured and which are obtained by means of the sensor apparatus, the spectral course of the radiation to be measured can be determined.

2. Apparatus in accordance with claim 1, characterized in that the number of N1 and N2 are greater than 1, that is, at least two radiant sources are provided which have spectral characteristics which overlap and are linearly independent of each other and that the number of M1 and M2 are equal to 1, that is, a sensor is provided which is sensitive to the whole predetermined wavelength range.

3. Apparatus in accordance with claim 1, characterized in that the number of N1 and the number of N2 are 1, that is, only one radiant source is required whose radiation spans the predetermined wavelength range and that the number of M1 and M2 are at least equal to 2, that is, at least two sensors are provided whose characteristics overlap at least partially in such a way that the entire predetermined wavelength range is covered and the characteristics are linearly independent of one another.

4. Apparatus in accordance with claim 2, characterized in that the number of N2 and M2 are greater than 1 respectively.

5. Apparatus in accordance with claim 1, characterized in that the radiant source emits the radiation to be measured and that the predetermined wavelength range is the wavelength range in which the radiation emitted from the illumination source is to be detected.

6. Apparatus in accordance with claim 1, characterized in that within the predetermined wavelength range a number x, preferably equidistant values are provided and that the calibration functions are generated in such a way that the spectral distribution of the radiation to be measured is determined from said values x.

7. Apparatus in accordance with claim 6, characterized in that said calibration functions are determined at each of said values x in that a set of linear equations is solved which contains p equations with p unknown coefficients.

8. Apparatus in accordance with claim 1, characterized in that said apparatus is provided with a measuring head in which said radiant source or radiant sources and said sensor or sensors are fitted.

9. Apparatus in accordance with claim 8, characterized in that said measuring head is in the form of a bell which is provided with an aperture for measuring, along with which the bell can be placed on top of the area to be measured, and that said radiant sources and/or said sensors are arranged in the cladding of said bell.

10. Apparatus in accordance with claim 1, characterized in that said radiant source is a lighting device.

11. Apparatus in accordance with claim 10, characterized in that said lighting device is a light emitting diode (LED).

12. Method for measuring an analyzing spectral radiation within a predetermined wave length range and in particular for detecting the characteristics of colors, comprising:

a number of N1 radiant sources which emit radiation which is distributed spectrally over a wavelength range which lies, at least partially, within said predetermined wavelength range, where the spectral characteristics of said individual radiant sources differ from one another and N1 is greater than or equal to 1, sensor apparatus which detects radiation within said predetermined wavelength range and generates an electrical signal which is representative of the intensity of the detected radiation, a control unit which controls the radiation of said apparatus and which causes the radiant sources to be actuated in predetermined combinations at successive intervals of time, a storage device, in which the values detected by means of the sensor apparatus for the respective combinations of radiant sources are recorded and stored, and the control unit calculates values from said stored values for identifying the spectral characteristics of the radiant sources, characterized in that the radiant sources are selected in such a way that their spectral characteristics overlap with said predetermined wavelength range, the spectral characteristics of the light sources furthermore are such that the characteristics of at least N2 of said light sources are linearly independent of one another, said sensor apparatus comprises a number of M1 sensors whose spectral characteristics in the predetermined wavelength range overlap in such a way that the entire predetermined wavelength range is covered, where M1 is greater than or equal to 1;

the spectral characteristics of the sensors are furthermore such that the characteristics of at least M2 of said radiant sources are linearly independent of one another, the product P=N2*M2 derived from the multiplication of the values for N2 and M2 is greater than 1;

in said storage device a number of P calibration functions are stored which span the predetermined wavelength range at least partially, and which define the relationship between the spectral intensity distribution of P standard samples, which is measured by means of the individual device, and their known reflectance spectrums, the spectral characteristics of the reflectance spectums being linearly independent of one another and overlapping, at least partially, in such a way that the entire wavelength range is recorded and that by combining said calibration functions with the measured values for the radiation to be measured and which are obtained by means of the sensor apparatus, the spectral characteristics of the radiation to be measured can be determined.

13. Method according to claim 12, characterized in that the number of N1 and N2 are greater than 1, that is, at least two radiant sources are provided which have spectral characteristics which overlap and are linearly independent of each other and that the number of M1 and M2 are equal to 1, that is, a sensor is provided which is sensitive to the whole predetermined wavelength range.

14. Method according to claim 12, characterized in that the number of N1 and the number of N2 are 1, that is, only one radiant source is required whose radiation spans the predetermined wavelength range and that the number of M1 and M2 are at least equal to 2, that is, at least two sensors are provided whose characteristics overlap at least partially in such a way that the characteristics are linearly independent of one another.

15. Method according to claim 13, characterized in that the number of N2 and M2 are greater than 1 respectively.

16. Method according to claim 12, characterized in that the radiant source emits the radiation to be measured and that the predetermined wavelength range is the wavelength range in which the radiation emitted from the illumination source is to be detected.

17. Method according to claim 12, characterized in that within the predetermined wavelength range a number x, preferably equidistant values are provided and that the calibration functions are generated in such a way that the spectral distribution of the radiation to be measured is determined from said values x.

18. Method according to claim 17, characterized in that said calibration functions are determined at each of said values x in that a set of linear equations is solved which contains p equations with p unknown coefficients.

* * * * *